US00PP34107P2

(12) United States Plant Patent
Snijder

(10) Patent No.: US PP34,107 P2
(45) Date of Patent: Apr. 5, 2022

(54) ***PELARGONIUM* PLANT NAMED 'PEQZ0084'**

(50) Latin Name: ***Pelargonium* interspecific**
Varietal Denomination: PEQZ0084

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/366,286

(22) Filed: Jul. 2, 2021

(51) Int. Cl.
*A01H 5/02* (2018.01)
*A01H 6/42* (2018.01)

(52) U.S. Cl.
USPC ..... Plt./330
CPC ..... *A01H 6/425* (2018.05)

(58) Field of Classification Search
USPC ..... Plt./330
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0084' particularly distinguished by large scarlet red colored inflorescences with large semi-double florets, held above dark green foliage, on a vigorous upright-mounding plant.

1 Drawing Sheet

Latin name of the genus and species of the plant claimed: *Pelargonium* interspecific.

Varietal denomination: 'PEQZ0084'.

BACKGROUND OF THE NEW PLANT

The present invention comprises a new *Pelargonium*, botanically known as *Pelargonium* interspecific, and hereinafter referred to by the variety name 'PEQZ0084'.

'PEQZ0084' is a product of a planned breeding program. The new cultivar 'PEQZ0084' has large scarlet red colored inflorescences with large semi-double florets, held above dark green foliage, on a vigorous upright-mounding plant.

'PEQZ0084' originates from a hybridization in a controlled breeding program made in July 2015, in a greenhouse in Enkhuizen, The Netherlands. The female parent was an unpatented plant of *P.* x interspecific parentage identified as 'PEZ-AZ3236-03V' with lighter, medium green, foliage and single florets when compared to 'PEQZ0084'.

The male parent of 'PEQZ0084' was an unpatented, proprietary plant of *P.* x *hortorum* parentage, identified as 'PEZ-AZ3272-07V' with a more upright and compact plant habit when compared to 'PEQZ0084'. The resultant seed was sown in December 2015.

'PEQZ0084' was selected as one flowering plant within the progeny of the stated cross in May 2016 in a greenhouse in Enkhuizen, The Netherlands.

The first act of asexual reproduction of 'PEQZ0084' was accomplished when vegetative cuttings were propagated from the initial selection in June 2016 in a greenhouse in Enkhuizen, The Netherlands.

BRIEF SUMMARY OF INVENTION

Horticultural examination of plants grown from cuttings of the plant initiated in May 2016 in Enkhuizen, The Netherlands and continuing thereafter, has demonstrated that the combination of characteristics as herein disclosed for 'PEQZ0084' are firmly fixed and are retained through successive generations of asexual reproduction.

'PEQZ0084' has not been observed under all possible environmental conditions. The phenotype may vary significantly with variations in environment such as temperature, light intensity, and day length.

A Plant Breeder's Right for this cultivar was applied for in the European Union on Jun. 14, 2021, No. 2021/1595. 'PEQZ0084' has not been made publicly available prior to the effective filing date of this application, notwithstanding any disclosure that may have been made less than one year prior to the effective filing date of this application by the inventor or another who obtained 'PEQZ0084' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
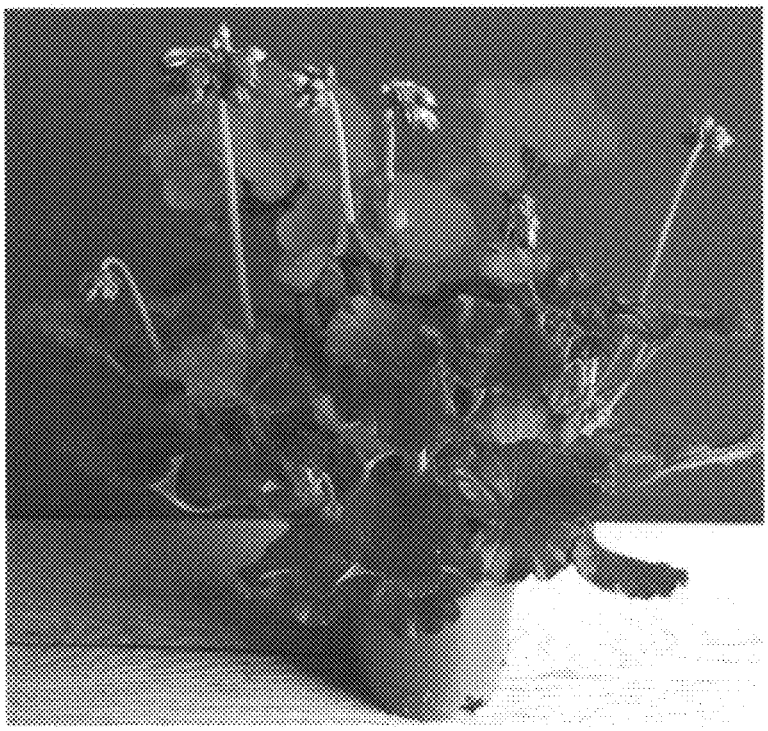
Figure 2:
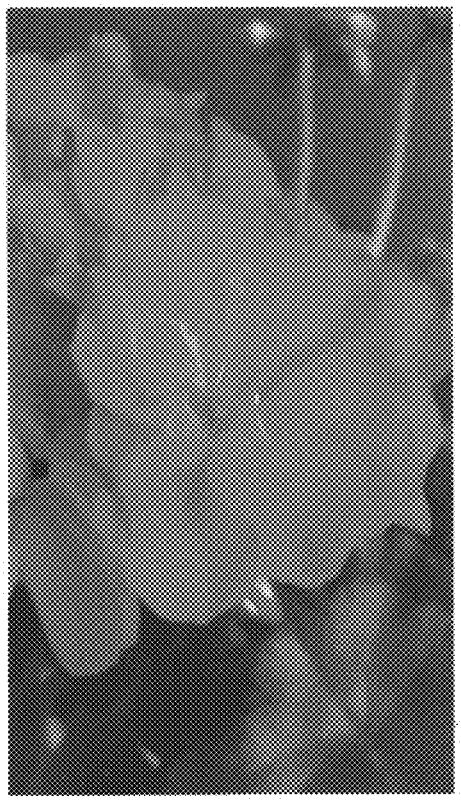

The accompanying photographic drawings show typical flower and foliage characteristics of 'PEQZ0084' with colors being as true as possible with an illustration of this type. The photographic drawings show in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in early June 2021 under natural light. These plants were approximately 16 weeks old and were grown in a 12 cm pots, in a greenhouse trial. The plants shown in the photographs were about 16 weeks old growing in a 12 cm pot in a greenhouse. The photographs were taken in June 2021.

Color references are made to The Royal Horticultural Society Colour Chart (R.H.S.) 2001.

TABLE 1

DIFFERENCES BETWEEN THE NEW VARIETY 'PEQZ0084' AND A MOST SIMILAR VARIETY

| | 'PEQZ0084' | 'FISROCKY DARK RED' (U.S. Plant Pat. No. 12,237) |
|---|---|---|
| Plant size: | Upright-mounding large | Upright small compact |
| Peduncle length: | Long: 20-24 cm | Shorter: 12.8 cm |

Plant:

*Form, growth and habit.*—Upright-mounding growth habit.

*Plant height.*—18-20 cm.

*Plant height (inflorescence included).*—35-38 cm.

*Plant width.*—26-39 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Variegation.*—Absent.

*Immature leaf, color upper surface.*—Between RHS 137A and RHS 139A.

*Immature leaf, lower surface.*—Closest to RHS 138B.

*Mature leaf, color upper surface.*—RHS 139A.

*Mature leaf, color lower surface.*—RHS 138A.

*Length.*—7-9 cm.

*Width.*—8.5-11.5 cm.

*Shape.*—Cordate-reniform.

*Base shape.*—Cordate.

*Sinus of mature leaf.*—Very narrow.

*Leaf base openness.*—Almost closed or slightly open.

*Apex shape.*—Rounded.

*Margin.*—Slightly dentate.

*Texture upper side.*—Hirsute.

*Texture lower side.*—Hirsute.

*Leaf zonation color.*—Slightly darker than RHS 139A.

*Color of veins, upper surface.*—RHS 137A, largely indistinct.

*Color of veins, lower surface.*—RHS 144D, becoming indistinct.

*Pattern of veining.*—Palmate.

*Petiole color.*—RHS 143C.

*Petiole length.*—6.5-8.5 cm.

*Diameter of petiole.*—0.3 cm.

*Texture.*—Pilose, hirsute, glandular hairs.

Stem:

*Quantity of branches.*—5-9.

*Color of stem.*—RHS 143C.

*Anthocyanin coloration of stem.*—A weak anthocyanin coloration is visible under high solar radiation.

*Length of stem.*—6-16 cm.

*Diameter.*—0.5-0.8 cm.

*Length of internodes.*—1-3.5 cm.

*Texture.*—Sparsely hirsute, pilose, glandular hairs.

Peduncle:

*Color of peduncle.*—RHS 144A, fading to RHS 176B at upper half.

*Length of peduncle.*—20-24 cm.

*Peduncle diameter.*—0.3-0.5 cm.

*Texture.*—Hirsute, glandular hairs.

*Anthocyanin coloration of peduncle.*—Anthocyanin coloration is visible under high solar radiation on upper half.

Pedicel:

*Color of pedicel.*—RHS 185A.

*Length of pedicel.*—3-3.5 cm.

*Diameter of pedicel.*—0.15-0.2 cm.

*Texture.*—Sparsely pilose, glandular hairs.

*Pedicel swelling.*—Swelling was not observed.

Bud (just before opening):

*Color.*—Between RHS 45A and 46A.

*Length.*—1.5-1.7 cm.

*Width.*—0.8-1.0 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—6-12, with 5-12 immature umbels in various stages.

*Average total number of buds.*—18.

*Fragrance.*—None.

*Umbel diameter.*—10-12 cm.

*Umbel depth.*—8-9 cm.

Corolla:

*Form.*—Semi-double.

*Number of petals.*—6-8.

*Diameter of flower.*—5.5-6.5 cm.

*Depth of flower.*—2-2.5 cm.

*Side view shape.*—Concave.

*Color upper petals, upper surface.*—between RHS 44B and RHS 45A with veins RHS 53B and a slight.

*Color upper petals, lower surface.*—RHS 40A.

*Length of upper petals.*—2.8-3.0 cm.

*Width of upper petals.*—2.5-2.7 cm.

*Color lower petals, upper surface.*—Between RHS 44B and RHS 45A.

*Color lower petals, lower surface.*—RHS 40A.

*Markings on upper petals.*—Veins RHS 45A.

*Markings on lower petals.*—None.

*Length of lower petals.*—2.7-3.0 cm.

*Width of lower petals.*—2.4-2.6 cm, petaloids variably smaller and with variable shape.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144C, base RHS 185A.

*Length of sepals.*—1.3-1.4 cm.

*Width of sepals.*—0.2-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

*Sepal flexing.*—Mostly unflexed sepals. The narrowest sepals might flex moderately.

Reproductive organs:

Gynoecium:

*Pistil.*—RHS 71A.

*Length.*—0.8-0.9 cm.

*Style color*.—RHS 71A.
*Style length*.—0.3 cm.
*Stigma color*.—RHS 71A.
*Ovary color*.—RHS 71A.
*Ovary length*.—0.5 cm.
*Ovary diameter*.—0.2 cm.

Androecium:

*Number of stamens*.—6-9.
*Color of filaments*.—RHS N155A, N57C at apex.
*Length filaments*.—0.6-0.7 cm.
*Anther color*.—RHS 58B.
*Length of anthers*.—0.2-0.3 cm.
*Color of pollen*.—RHS N171B.
*Pollen amount*.—Abundant.
*Fertility/seed set*.—Has not been determined to date.
*Disease/pest resistance*.—Has not been determined to date.

What is claimed is:

1. A new and distinct variety of *Pelargonium* plant named 'PEQZ0084' substantially as illustrated and described herein.

* * * * *